April 18, 1972 A. TAYLOR Plant Pat. 3,121
APPLE TREE
Filed April 16, 1970
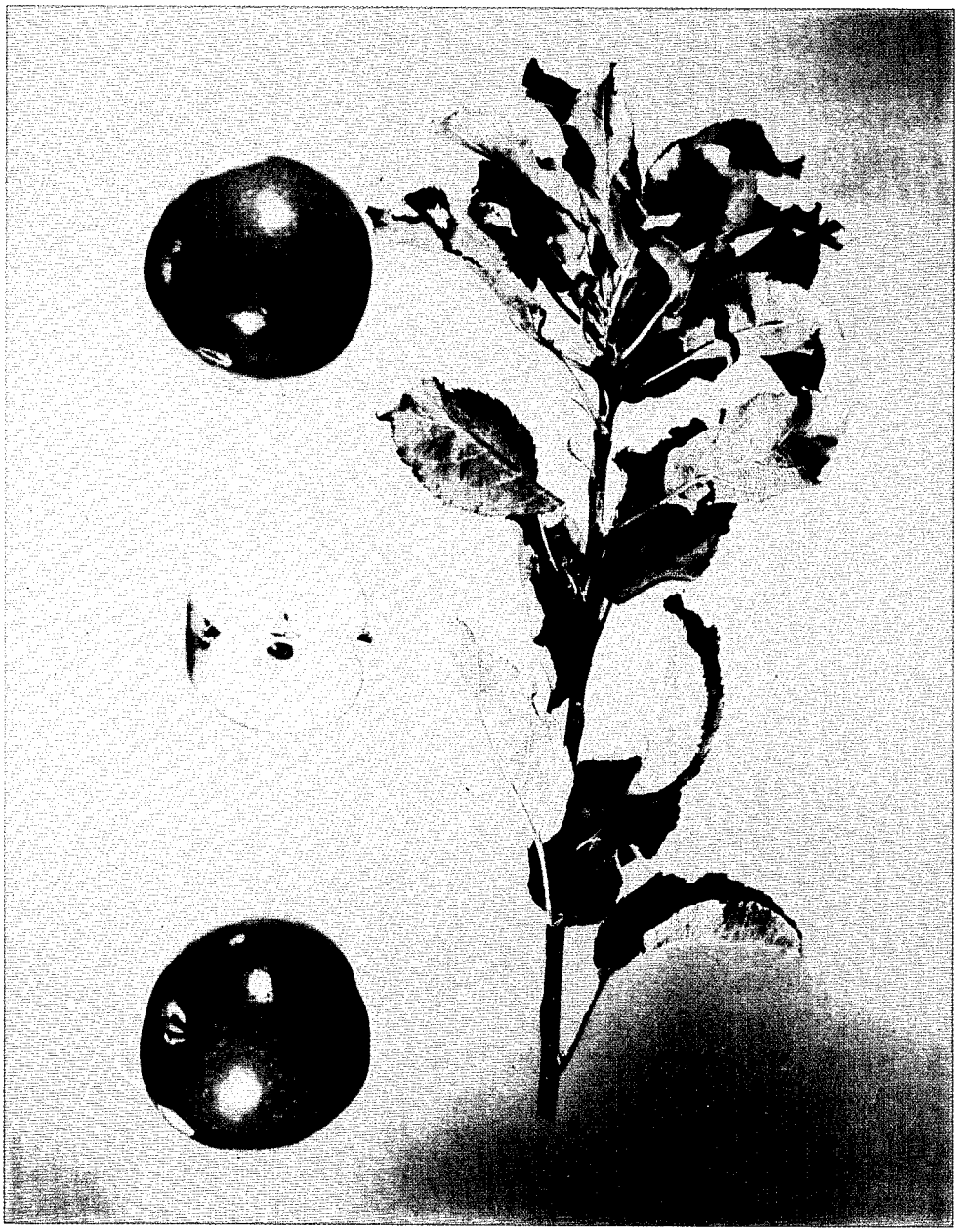
Inventor.
Alvah Taylor
By: Robb & Robb
Attorneys.

United States Patent Office

Plant Pat. 3,121
Patented Apr. 18, 1972

3,121
APPLE TREE

Alvah Taylor, Selah, Wash., assignor to Stark Bro's Nurseries & Orchards Company, Louisiana, Mo.

Filed Apr. 16, 1970, Ser. No. 29,310
Int. Cl. A01h *5/03*
U.S. Cl. Plt.—34 1 Claim

The present invention relates to a new and distinct variety of apple tree which was discovered by me as a bud mutation or limb sport of the old standard apple variety commonly known as "Rome Beauty" (unpatented), said discovery having been made by me in my cultivated orchard on my property situated at Selah, in Yakima County, Wash.

At the time of my discovery, I was growing in my orchard aforesaid trees of the "Rome Beauty" variety aforementioned. In the course of a routine inspection of this orchard, my attention was attracted to a particular limb on one tree which bore fruit that was more brightly colored much earlier than the fruit on the remainder of the tree and on all other trees in the orchard. Close inspection and prolonged observation of the limb indicated that it was a sport, and I therefore took steps to carefully preserve the same and keep it under close observation. In due course, I asexually reproduced the mutation by grafting, as performed by me in the same orchard at Selah, Wash.

Continued observations of the original sport limb and the progeny derived therefrom by grafting, as stated above, have convinced me that it is a new and distinct variety, as particularly evidenced by the following unique combination of characteristics which are outstanding therein and which distinguish it from its parent variety "Rome Beauty" and from all other apple varieties of which I am aware, including all other strains of "Rome Beauty" now in commerce:

(1) A general resemblance to the parent variety "Rome Beauty" but having
(2) More upright, less weeping and thicker limbs;
(3) A much heavier fruit spur system throughout the tree;
(4) A habit of beginning the production of fruit at an earlier age, with continued heavy production thereafter;
(5) An earlier fruit coloring habit, with the fruit color being fully developed as a full blush without stripes by the time of harvest maturity and usually grading substantially 100% "extra fancy" for color; and
(6) A distinctive, attractive, full and bright cherry red fruit color completely free of striping.

The accompanying drawing shows typical specimens of the foliage as borne on a typical branch section, as well as typical specimens of the fruit, and with one of the fruit specimens being shown in cross section, all as depicted in color as nearly true as it is reasonably possible to make the same in a color illustration of this character.

The following is a detailed description of my new variety, with color terminology in accordance with Munsell Color Chart (hereinafter abbreviated as (M)), and the Horticultural Colour Guide (hereinafter abbreviated as (HCG)), as indicated, except where general color terms of ordinary dictionary significance are obvious:

Locality where grown and observed: Selah, Wash.
Dates of first and last pickings: About October 20 and November 1, respectively.
Tree: Medium small; medium vigorous; upright; tall; slow growing; hardy; very productive; regular bearing.
*Trunk.*—Medium stocky; medium smoooth.
*Branches.*—Medium thickness; smooth; much branched. Color — brown. Lenticles — medium number; medium size.
*Leaves.*—Medium large; medium width; medium length; oval; taper-pointed; medium thickness; smooth. Length—about 3⅝ inches. Width—about 2¼ inches. Color—Spinach Green, Plate 0960/1, page 187, vol. 2 (HCG). Margin—finely serrate. Petiole—medium length; medium slender.
Flowers:
*Dates of first and full bloom.*—About May 6 and May 12, respectively; late as compared with other varieties.
*Color.*—White.
Fruit:
*Maturity when described.*—Hard-ripe; about November 1.
*Size.*—Uniform. Axial diameter—about 3 inches. Transverse diameter—about 3½ inches.
*Form.*—Truncate at base; round-conical; characteristically obtuse and smooth.
*Cavity.*—Symmetrical; flaring toward apex; even. Depth—about 5/16 inch. Breadth—about 1¼ inches. Markings—none.
*Basin.*—Symmetrical; rounded; furrowed; pubescent. Depth—about ¼ inch. Breadth—about 1 inch. Markings—none.
*Stem.*—Clubbed; medium stout; pubescent. Length—about ¾ inch; shorter than "Rome Beauty". Breadth—about 1/16 inch. Markings—none.
*Calyx.*—Open; segments persistent; narrowly lanceolate; about 5/16 inch long; separated at base; ascending; converged from base toward center; both outer and inner surface pubescent.
*Eye.*—Medium size; open.
*Skin.*—Thick; tough; smooth; glossy; waxed. Dots—obsecure; many; small; depressed; circular. Color—cream, tinged with pink. Distribution—mostly toward calyx basin. Ground color—brillant yellow green, Hue 2.5 GY 9/8 (M). Color markings—blushed; self-colored; bright. Color—strong red, Hue 5 R 4/12 (M). Bloom—wanting. Scarfskin—wanting. General color effect—bright strong red all over solid blush type red pigmentation.
*Flesh.*—Rather juicy. Color—yellowish green tint. Texture—firm; fine; crisp. Flavor—subacid; mild. Aroma—wanting. Quality—good.
*Core.*—Median. Bundle area—medium large; cordate; symmetrical; acute at base. Halves of core area—equal. Bundles—conspicuous; in one whorl. Color—Greenish yellow. Core lines—clasping. Calyx tube—pubescent toward base; broadly obconic. Entire depth—about ¼ inch. Styles—present; fleshy at base; united toward base; glabrous toward base. Stamens—in one distinct whorl. Auxiliary cavity—present. Seed cells—axile; open. Cell walls—distant; thick; tough. Length—about ¾ inch. Breadth—about ¼ inch. Longitudinal section—orbicular; emarginate. Surface—fissured. Cross section—broad.
Seeds: Usually 8 and all perfect; usually 2 per cell.
*Length.*—About ⅜ inch.
*Breadth.*—About ⅛ inch.
*Form.*—Acute.
*Color.*—Moderate Reddish Brown, Hue 2.5 YR 3/3 (M).
Use: Market; dessert; culinary.
Keeping quality: Good; about 135 days in refrigerated storage.
Insect and disease resistance: Good insect resistance and medium disease resistance as determined by comparison with the effect of the usual apple insects and diseases on other apple varieties grown under the same conditions at Selah, Wash.

I claim:

1. A new and distinct variety of apple tree, substantially as herein shown and described, characterized particularly as to novelty by the unique combination of a general resemblance to the parent variety "Rome Beauty" (unpatented), but having more upright, less weeping and thicker limbs, a much heavier fruit spur system throughout the tree, a habit of beginning the production of fruit at an earlier age, with continued heavy production thereafter, an earlier fruit coloring habit, with the fruit color being fully developed as a full blush without stripes by the time of harvest maturity and usually grading substantially 100% "extra fancy" for color, and a distinctive, attractive, full and bright cherry red fruit color completely free of striping.

No references cited.

ROBERT E. BAGWILL, Primary Examiner